United States Patent
Han et al.

(10) Patent No.: US 7,820,429 B2
(45) Date of Patent: Oct. 26, 2010

(54) METHOD FOR DRY FERMENTATION AND EQUIPMENT FOR CARRYING OUT THE SAME

(75) Inventors: Jie Han, Beijing (CN); Yuhua Zhang, Beijing (CN); Tong Chen, Beijing (CN); Xin Xiang, Beijing (CN)

(73) Assignee: Chinese Academy of Agricultural Engineering, Beijing (CN)

( * ) Notice: Subject to any disclaimer, the term of this patent is extended or adjusted under 35 U.S.C. 154(b) by 956 days.

(21) Appl. No.: 11/571,175

(22) PCT Filed: Jul. 14, 2005

(86) PCT No.: PCT/CN2005/001046
§ 371 (c)(1),
(2), (4) Date: Dec. 22, 2006

(87) PCT Pub. No.: WO2006/005266
PCT Pub. Date: Jan. 19, 2006

(65) Prior Publication Data
US 2008/0248541 A1    Oct. 9, 2008

(30) Foreign Application Priority Data
Jul. 14, 2004 (CN) .................... 2004 1 0071598
Jul. 11, 2005 (CN) .................... 2005 1 0082723

(51) Int. Cl.
*C12M 1/00* (2006.01)
*C12M 3/00* (2006.01)
*C12M 1/02* (2006.01)
*C12M 1/10* (2006.01)

(52) U.S. Cl. .............. 435/289.1; 435/290.1; 435/290.2; 435/290.4

(58) Field of Classification Search ................ 435/289.1
See application file for complete search history.

(56) References Cited

U.S. PATENT DOCUMENTS
4,436,818 A * 3/1984 Widmer .................. 435/290.2

(Continued)

FOREIGN PATENT DOCUMENTS
CN         A 1480523         3/2004

(Continued)

*Primary Examiner*—Walter D Griffin
*Assistant Examiner*—Lydia Edwards
(74) *Attorney, Agent, or Firm*—Gottlieb, Rackman & Reisman, PC

(57) ABSTRACT

The present invention relates to a method for dry fermentation and equipment for carrying out the same. The invention equipment comprises a fermentation tank for dry fermentation which includes a tank body 5 for accommodating materials, a flexible sealing membrane 7 for covering said tank body 5, and a tight fixing means 3 for hermetically covering the tank body 5 with the flexible sealing membrane 7. This invention is characterized in that said tank body 5 is provided with a top opening 2 at its top part and at least one side opening 4 for loading and unloading materials at its side portions. When the tank body 5 is covered hermetically by the flexible sealing membrane 7, said tight fixing means 3 makes the contact area 6 between the tank body 5 and the flexible sealing membrane 7 form at least one sealing contacting strip or at least one sealing line which is continuous and close in three-dimensional space so that the flexible sealing membrane 7 covers hermetically both the top opening 2 and at least one side opening 4 for loading and unloading materials.

4 Claims, 3 Drawing Sheets

U.S. PATENT DOCUMENTS

2006/0188980 A1 * 8/2006 Holtzapple et al. ....... 435/290.1

FOREIGN PATENT DOCUMENTS

| | | | |
|---|---|---|---|
| EP | A2 | 0056202 | 7/1982 |
| EP | A2 | 0521302 | 1/1993 |
| EP | A1 | 1136546 | 9/2001 |
| FR | A2 | 2500716 | 9/1982 |

* cited by examiner

METHOD FOR DRY FERMENTATION AND EQUIPMENT FOR CARRYING OUT THE SAME

TECHNICAL FIELD

The present invention in general relates to a method for dry fermentation and equipment for carrying out the same.

BACKGROUND ART

It is well known in the art that anaerobic fermentation can be classified roughly into two classes: wet fermentation and dry fermentation. Wet anaerobic fermentation is widely used to produce biogas by means of the liquid waste materials, such as animal manure and yeast wash, etc. If wet anaerobic fermentation is used to produce biogas in cold regions, it consumes large amounts of energy, and thereby the economic benefit is less, even more, the loss is more than the gain.

In the past, dry anaerobic fermentation was mostly used in the brewing industry. But recently, study on the treatment of solid organic waste utilizing dry anaerobic fermentation is developing in China and abroad, which can help to produce organic fertilizer while obtaining clean energy (biogas). At the present stage, there are cylinder type and chamber type constructions. The cylinder type construction is difficult for loading and unloading materials and involves an extremely high cost. As for the chamber type construction, it is required to transport materials several times, that is, materials are at first pre-treated to raise temperature through aerobic fermentation, and then transported into the anaerobic fermentation chamber to produce biogas, after that, they go to the plant for producing organic fertilizer to be processed. The process by making use of the chamber type construction requires much labour and time. Also, the space for the chamber type construction is large, and the manufacturing accuracy of the sealing door of the anaerobic fermentation chamber and the demand for explosion-proof monitoring are both high.

SUMMARY OF THE INVENTION

In order to overcome the above-mentioned disadvantages of the prior art technology, an object of the invention is to provide a method for dry fermentation and equipment for carrying out the same, which can produce biogas and organic fertilizer through anaerobic fermentation and aerobic fermentation by making use of solid organic waste. The benefits of the invention method and equipment lie in that the process is simple and low energy cost, the equipment is easy to load and unload materials and small in scale so that the cost thereof is decreased.

The invention equipment comprises a fermentation tank for dry fermentation which includes a tank body for accommodating materials, a flexible sealing membrane for covering said tank body, and a tight fixing means for hermetically covering the tank body with the flexible sealing membrane. This invention is characterized in that said tank body is provided with a top opening at its top part and at least one side opening for loading and unloading materials at its side part. When the tank body is covered hermetically by the flexible sealing membrane, said tight fixing means makes the contact area between the tank body and the flexible sealing membrane form at least one sealing contacting strip or at least one sealing line which is continuous and close in three-dimensional space so that the flexible sealing membrane covers hermetically both of the top opening and at least one side opening for loading and unloading materials, wherein said tight fixing means can be a tight fixing means in the form of inflatable soft pipe-channels.

The shape and the size of the top opening are required to satisfy the following requirements: operation device (such as stirring device) can take mechanized operations (e.g. stirring) to materials via said top opening during the process of aerobic fermentation.

The side opening for loading and unloading materials should be convenient for the loading and unloading device to carry out the loading and unloading operations.

In a preferable embodiment of die invention, the top opening and tire side opening for loading and unloading materials can be connected to each other to form only one opening or separated from each other.

The above-mentioned tank body includes two parallel side walls and a side wall which is perpendicular to said parallel side walls. The top surface and one side surface of the tank body are opened to form the top opening and the side opening for loading and unloading materials, respectively. When the tank body is covered hermetically by the flexible sealing membrane, at least one sealing contacting strip or at least one sealing contacting line which is continuous and close in three-dimensional space is formed on the contact area between the tank body and the flexible sealing membrane by said tight fixing means, so that the top opening and at least one side opening for loading and unloading materials are hermetically covered by the flexible sealing membrane.

Said tight fixing means can be a tight fixing means in the form of inflatable soft pipe-channels.

Rails can be provided at the top of the two parallel side walls of the tank body. During the process of aerobic fermentation, stirring device or another operation device can move along the rails and carry out the operations, for example, stirring materials in the fermentation tank.

A loader can be used to load and unload materials conveniently through the side opening for loading and unloading materials.

One of the methods for processing solid organic waste through fermentation, process by making use of the equipment according to the present invention is that: both of the top opening and the side opening for loading and unloading materials of the tank body for containing solid organic waste are covered hermetically by the flexible sealing membrane, so that the solid organic waste in the tank body is subject to "anaerobic gas-forming" fermentation process which can produce biogas.

In an exemplary embodiment in accordance with this invention, one of the methods for processing solid organic waste through fermentation process by making use of the equipment according to the present invention is that: before the above-mentioned process of "anaerobic gas-forming" fermentation, the solid organic waste in the tank body is subject to the process of "aerobic temperature-rising" fermentation. Aerobic fermentation process can make the temperature of materials in the tank body rise, and the anaerobic fermentation process can produce biogas.

One of the methods for processing solid organic waste through fermentation process by making use of the equipment according to the present invention is that: after the above-mentioned process of "anaerobic gas-forming" fermentation, the solid organic waste in the tank body is subject to the process of "aerobic fertilizer-producing" fermentation. Anaerobic fermentation process can produce biogas, and aerobic fermentation process can produce organic fertilizer.

One of the methods for processing solid organic waste through fermentation process by making use of the equipment according to the present invention is that: before said "anaerobic gas-forming" fermentation process, the solid organic waste in the tank body is subject to the process of "aerobic temperature-rising" fermentation; and after said "anaerobic gas-forming" fermentation process, the solid organic waste in the tank body is subject to the process of "aerobic fertilizer-producing" fermentation.

A common feature of the above four methods lies in that, both of the top opening and the side opening for loading and unloading materials of the tank body are open during the aerobic process; and both of the top opening and the side opening for loading and unloading materials of the tank body are covered hermetically by the flexible sealing membrane during the anaerobic process.

A plurality of fermentation tank bodies can be arranged simultaneously, and fermentation process can be carried out with a plurality of tank bodies in a sequence of equal time interval. Since the fermentation, cycles in every fermentation tank are equal, the output of biogas can be maintained continuously and stably by doing so.

The present invention can be widely applied to the treatment of many kinds of the organic wastes such as animal manure, crop stalk, and household garbage. With the equipment and the method according to the present invention, on the one hand, the environment pollution from the organic waste can be decreased; on the other hand, recycled, clean energy (biogas) and organic fertilizer can be produced.

The present invention involves three stages of single tank fermentation process, which are aerobic temperature-rising stage, anaerobic gas-forming stage and aerobic fertilizer-producing stage. With this process, the floor space for the equipment, investment cost and man-hour can all be decreased efficiently.

The present invention can fully exploit the solar energy and the biological energy created by the aerobic fermentation of materials to make the temperature of materials rise and to maintain a "moderate temperature" condition with the aid of the self-thermal insulation property of deep stack materials when materials are subject to said "anaerobic gas-forming" fermentation process, thereby the gas output of the system can be increased efficiently.

The present invention includes the process of multiple-tank fermentation mode, in which a plurality of fermentation tanks supply biogas simultaneously in different periods for producing biogas. In this regard, the gas output of the whole system has little fluctuation, and the biogas can be output smoothly.

According to the present invention, anaerobic fermentation can be achieved by covering the fermentation tank with flexible sealing membrane. By doing so, it can be determined visually whether there is biogas in the gas bag or not, thereby the accident of the explosion caused by the remaining biogas can be prevented and the difficulty of safe handling of the biogas production can be decreased. Therefore, the safe monitoring system can be simplified so that the investment cost is lowered and the economical efficiency and practicability can be improved.

DETAILED DESCRIPTION OF THE PREFERRED EMBODIMENTS

Figure 1:
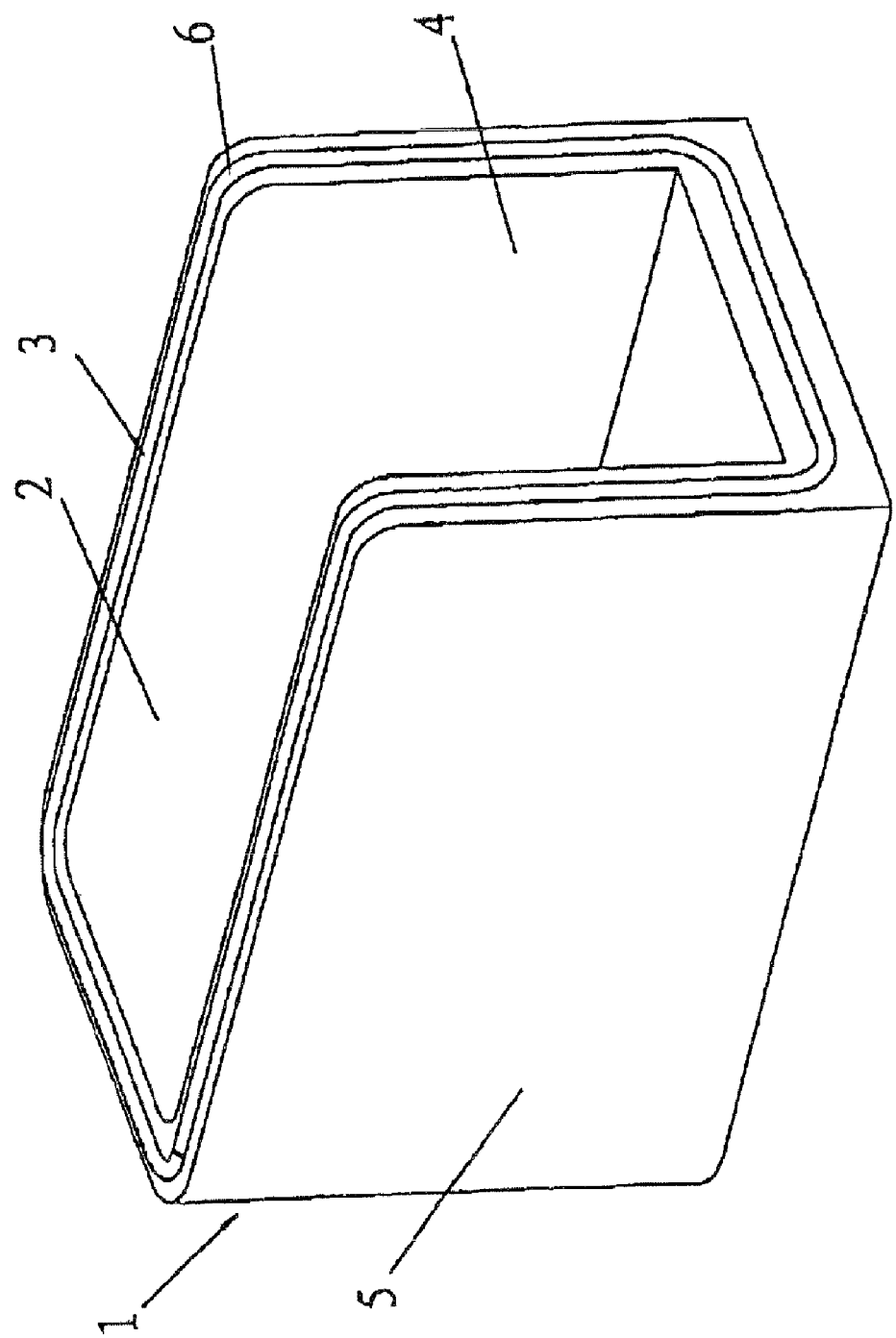
FIG. 1 is a perspective view of the fermentation tank according to the invention, which is not covered with the flexible sealing membrane.
Figure 2:
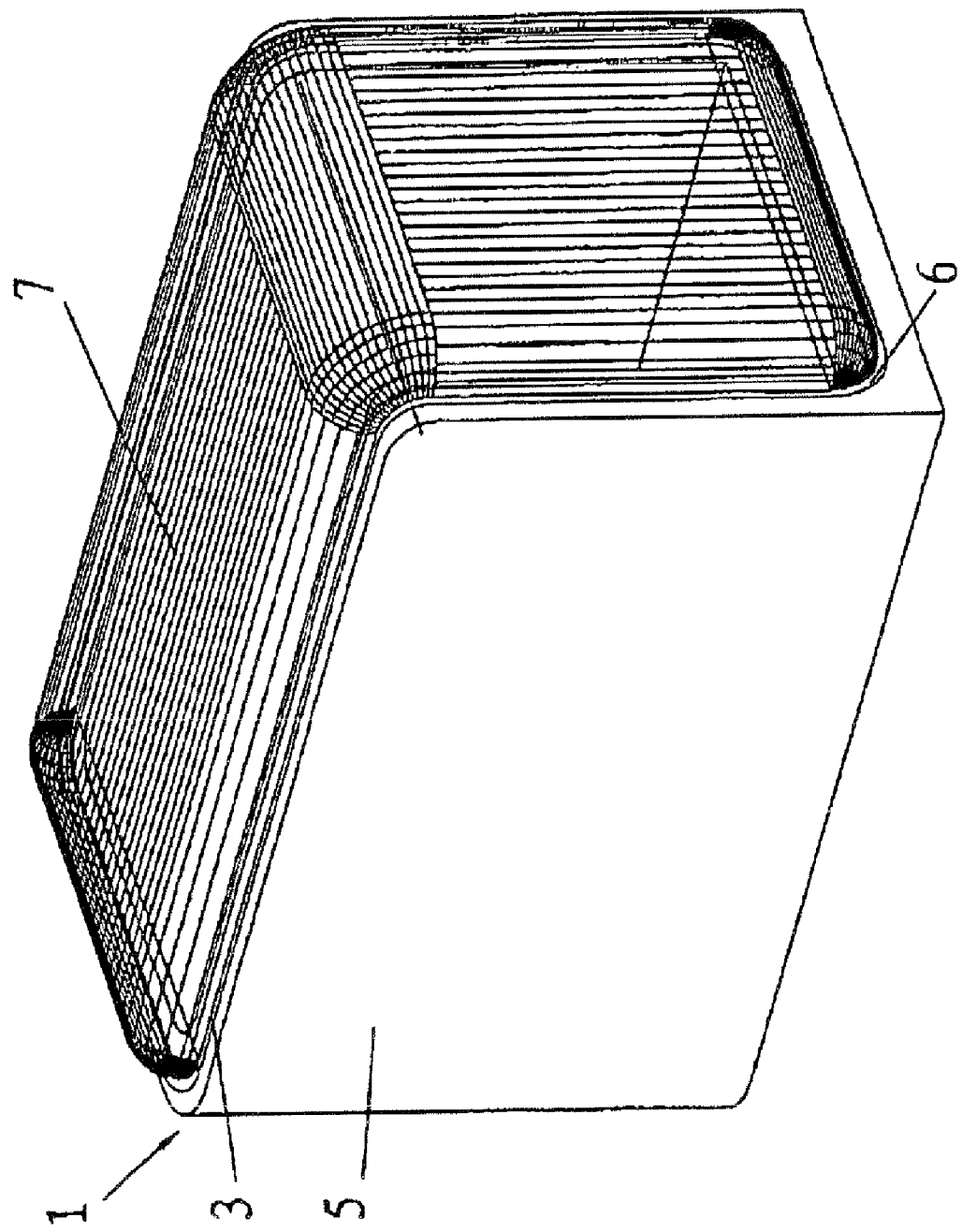
FIG. 2 is a perspective view of the fermentation tank according to the invention, which is covered with the flexible sealing membrane.

In FIGS. 1 and 2, the preferred embodiments of the present invention are shown, in which a tank body 5 is formed of two parallel side walls and a side wall which is perpendicular to said parallel side walls. The top and one side of a tank body 5 are open to form a top opening 2 and a side opening 4 for loading and unloading materials, respectively. When the tank body 5 is covered hermetically by a flexible sealing membrane 7, a tight fixing means 3 makes a contact area 6 between the tank body 5 and the flexible sealing membrane 7 form at least one sealing contacting strip or at least one sealing line which is continuous and close in three-dimensional space, so that the flexible sealing membrane 7 covers hermetically both of the top opening 2 and at least one side opening 4 for loading and unloading materials.

Among those, the tight fixing means 3 can be in the form of inflatable soft pipe-channels.

Moreover, the top opening 2 has the same area as that of the bottom surface of the tank body 5. During the process of aerobic fermentation, operation device (e.g. agitating and mixing vehicle 8) can do the mechanized operations (e.g. agitation) with respect to materials via said top opening 2.

The side opening 4 for loading and unloading materials is an opening which is completely open so that a mechanical loading and unloading device, such as a loader, can load and unload materials conveniently.

The top opening 2 and the side opening 4 for loading and unloading materials can connect each other in three-dimensional space to form one opening so that it is easy to construct the tank body 5 and do the loading and unloading operation.

Figure 3:
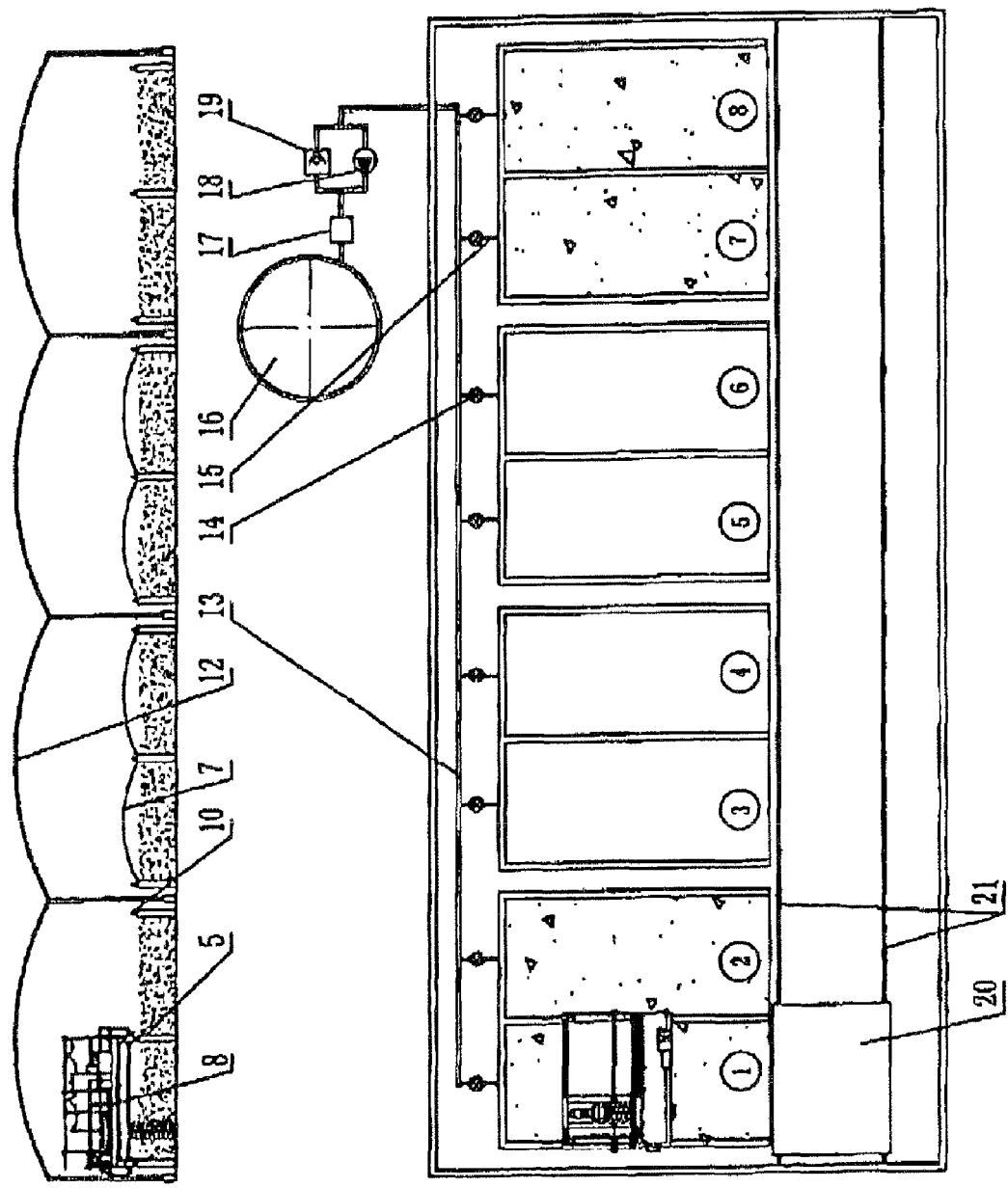
FIG. 3 is a diagram of the arrangement of the process, in which fermentation process is carried out with a plurality of tank bodies in a sequence of equal time interval.

As shown in FIG. 3, a plurality of fermentation tank bodies 5 can be provided depending on the materials handling capacity and the biogas demand. Each of the fermentation tank body 5 has one open end. Rails 10, along which an agitating and mixing vehicle 8 can move, are provided on the side walls of each fermentation tank body 5. A transporting device 20 is disposed at one end of the fermentation tank body 5 and can move along two rails 21 disposed in a direction orthogonal to the lengthwise direction of the fermentation tank body 5. The transporting device 20 can transport the agitating and mixing vehicle 8 from one fermentation tank 1 to another. A gas-collecting manifold branch 15 for discharging biogas and a cut-off valve 14 are disposed at the side wall of each of the fermentation tank bodies. All of the gas-collecting manifold branches 15 join into a gas-collecting main line 13 which leads to a biogas holder 16 via a biogas purifier 17. The gas-collecting main line 13 branches two by-passes, one of which is provided with an air compressor 18, the other one is provided with a check valve 19. Tire flexible sealing membrane 7 provided on the fermentation tank body 5 can cover hermetically the fermentation tank body 5 and it also can be rolled up conveniently. All of the fermentation tanks 1 are built up in a conservatory 12 which has a good transparence.

For the sake of a clear description of the working principle of the present invention, all the fermentation tanks are numbered in order. After the tank No. 1 has been filled with materials, materials are agitated by the agitating and mixing vehicle 8 to be supplied with oxygen for the aerobic fermentation. When the temperature of materials reaches a certain value, culture for anaerobic fermentation is spilled uniformly in materials and mixed evenly by the agitating and mixing vehicle 8. After that, the agitating and mixing vehicle 8 is moved from tank No. 1 to tank No. 2. When tank No. 2 begins to be loaded with materials, tank No. 1 is covered hermetically by the flexible sealing membrane 7 and starts anaerobic fermentation to produce biogas. When the anaerobic fermentation period set for tank No. 1 is expired, the flexible sealing membrane 7 is rolled up, and then, materials are agitated by the agitating and mixing vehicle 8 for the second aerobic fermentations. After several days, the fully burnt organic fertilizer is discharged from the tank. Similarly, after tank No. 2 is subject to the process of "aerobic temperature-rising" fermentation and is added with culture for anaerobic fermentation, it is covered hermetically by the flexible sealing membrane 7 and the stage of anaerobic fermentation is carried out to produce biogas. Right at this time, tank No. 3 begins to be charged. The rest may be inferred.

The filling with materials should be started with the first tank body and the next one will be filled with materials every several days.

From the time when loaded into the fermentation tank, materials are subjected to three stages of fermentation, i.e., aerobic temperature-rising stage, anaerobic gas forming stage and aerobic fertilizer-producing stage, to complete the production of biogas and organic fertilizer. The three-stage fermentation process goes on in the same fermentation tank from the beginning to the end. The sum of the time of the two aerobic fermentation stages is equal to the time of the anaerobic fermentation stage.

A loader can be used to load and unload materials for every fermentation tank 1.

After the biogas has been produced, a gas bag is formed between the fermentation tank 1 and the flexible sealing membrane 7. When a certain pressure of the biogas in the tank has been reached, the biogas starts to pass through the gas-collecting manifold branch 15, the opened cut-off valve 14, the gas-collecting main line 13, the check valve 19 and the biogas purifier 17 orderly, and then flows into the biogas holder 16, or is supplied directly to the users of biogas. When the gas-producing period of anaerobic fermentation set for a certain fermentation tank is expired, the cut-off valves 14 disposed at the gas-collecting manifold branches 15 of the other tanks are closed firstly, and secondly the air compressor 18 is activated to suck out the biogas under the flexible sealing membrane 7 of this fermentation tank 1. When it is confirmed there is not biogas in the tank any more, the cut-off valve 14 of the gas-collecting manifold branch 15 of this tank is closed, and the cut-off valves 14 disposed at the gas-collecting manifold branches 15 of the other gas-producing tanks are opened. Afterwards, the flexible sealing membrane 7 of this fermentation tank 1 is rolled up. At this time, the conservatory 12 should keep good ventilation.

When every tank is filled with materials and starts to run normally, half of the fermentation tanks are in the period of anaerobic fermentation and gas production everyday.

1. fermentation tank
2. top opening
3. tight fixing means
4. side opening
5. tank body
6. contact area
7. flexible sealing membrane
8. agitating and mixing vehicle
10. rail
12. conservatory
13. gas-collecting main line
14. cut-off valve
15. gas-collecting manifold branche
16. biogas holder
17. biogas purifier
18. air compressor
19. check valve
20. transporting device
21. rail

The invention claimed is:

1. An equipment for dry fermentation, comprising a fermentation tank (1) for dry fermentation which includes a tank body (5) for accommodating materials, a flexible sealing membrane (7) for covering said tank body (5) and a tight fixing means (3) for hermetically covering said tank body (5) with said flexible sealing membrane (7), wherein:
   a. said tank body (5) is provided with a top opening (2) at its top part and at least one side opening (4) for loading and unloading materials at its side part;
   b. when the tank body (5) is covered hermetically by the flexible sealing membrane (7), said tight fixing means (3) makes the contact area (6) between the tank body (5) and the flexible sealing membrane (7) form at least one sealing contacting strip or at least one sealing line which is continuous and close in three-dimensional space so that the flexible sealing membrane (7) covers hermetically both of the top opening (2) and at least one side opening (4) for loading and unloading materials.

2. The equipment according to claim 1, wherein:
   a. said tank body (5) is formed of two parallel side walls and a side wall which is perpendicular to said parallel side walls, the top and one side of said tank body (5) are open and form said top opening (2) and said side opening (4) for loading and unloading materials, respectively;
   b. when the tank body (5) is covered hermetically by the flexible sealing membrane (7), said tight fixing means (3) makes the contact area (6) between the tank body (5) and the flexible sealing membrane (7) form at least one sealing contacting strip or at least one sealing line which is continuous and close in three-dimensional space so that the flexible sealing membrane (7) covers hermetically both of the top opening (2) and at least one side opening (4) for loading and unloading materials.

3. The equipment according to claim 1 or 2, wherein said tight fixing means (3) is a tight fixing means in the form of inflatable soft pipe-channels.

4. The equipment according to claim 3, wherein rails (10) are provided at the top of the two parallel side walls of said tank body (5).

* * * * *